United States Patent
Mou et al.

(10) Patent No.: US 12,419,580 B2
(45) Date of Patent: Sep. 23, 2025

(54) EXPANDABLE MEMBER FOR AN ELECTROPHYSIOLOGY CATHETER

(71) Applicant: Abbott Cardiovascular Systems Inc., Santa Clara, CA (US)

(72) Inventors: Julie Pham Mou, Newark, CA (US); Hugo Antonio Cobar, Sunnyvale, CA (US); Ernest Munoz, Des Moines, WA (US); Cynthia R. Lee, Belmont, CA (US); Lei Zhou, Fremont, CA (US); David Alves, Redwood City, CA (US); Steven Chang, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 245 days.

(21) Appl. No.: 17/748,915

(22) Filed: May 19, 2022

(65) Prior Publication Data

US 2022/0273241 A1    Sep. 1, 2022

Related U.S. Application Data

(63) Continuation of application No. 15/867,657, filed on Jan. 10, 2018, now Pat. No. 11,344,259.
(Continued)

(51) Int. Cl.
*A61B 5/287*    (2021.01)
*A61B 5/00*    (2006.01)
(Continued)

(52) U.S. Cl.
CPC ............ *A61B 5/6858* (2013.01); *A61B 5/287* (2021.01); *A61B 5/349* (2021.01); *A61B 18/1492* (2013.01)

(58) Field of Classification Search
CPC ..... A61B 5/287; A61B 5/6858; A61B 5/6859; A61B 18/1482; A61B 2018/00267;
(Continued)

(56) References Cited

U.S. PATENT DOCUMENTS

| | | |
|---|---|---|
| 4,699,147 A | 10/1987 | Chilson et al. |
| 5,311,866 A | 5/1994 | Kagan et al. |

(Continued)

FOREIGN PATENT DOCUMENTS

| | | |
|---|---|---|
| CN | 104812297 A | 7/2015 |
| JP | 2002253557 A | 9/2002 |

(Continued)

OTHER PUBLICATIONS

Japanese Notification of Reason for Rejection (Office Action) from related Japanese Application No. 2019-537287 mailed on Dec. 15, 2020, 6 pages including translation.
(Continued)

*Primary Examiner* — Eun Hwa Kim
(74) *Attorney, Agent, or Firm* — Kilpatrick Townsend & Stockton LLP

(57) ABSTRACT

Expandable electrophysiology catheters having electrodes mounted on splines of an expandable member are described. The splines of the expandable member include subsegments between a proximal location and a distal intersection at a central axis. The subsegments can include respective top-down profiles, and at least one of the top-down subsegment profiles is straight between the central axis and an adjacent top-down subsegment profile. The subsegments can be interconnected to extend continuously about the central axis from the proximal location to the distal intersection. Other embodiments are also described.

20 Claims, 10 Drawing Sheets

Related U.S. Application Data

(60) Provisional application No. 62/445,137, filed on Jan. 11, 2017.

(51) Int. Cl.
*A61B 5/349* (2021.01)
*A61B 18/14* (2006.01)

(58) Field of Classification Search
CPC .... A61B 2018/1435; A61B 2018/1407; A61B 17/221
See application file for complete search history.

(56) References Cited

U.S. PATENT DOCUMENTS

| | | | |
|---|---|---|---|
| 5,782,239 | A | 7/1998 | Webster, Jr. |
| 5,836,947 | A | 11/1998 | Fleischman et al. |
| 6,016,437 | A * | 1/2000 | Tu .................. A61B 18/1492 606/41 |
| 6,063,082 | A | 5/2000 | Devore et al. |
| 6,071,274 | A | 6/2000 | Thompson et al. |
| 6,146,379 | A | 11/2000 | Fleischman et al. |
| 7,022,920 | B2 | 4/2006 | Hulburt et al. |
| 7,269,453 | B2 | 9/2007 | Mogul |
| 7,340,307 | B2 | 3/2008 | Macguire et al. |
| 8,103,327 | B2 | 1/2012 | Harlev et al. |
| 8,364,235 | B2 | 1/2013 | Kordis et al. |
| 9,370,311 | B2 * | 6/2016 | Stewart .................. A61B 5/287 |
| 9,474,486 | B2 | 10/2016 | Eliason et al. |
| 9,820,664 | B2 | 11/2017 | Hoitink et al. |
| 11,246,656 | B2 | 2/2022 | Harlev et al. |
| 2006/0111703 | A1 | 5/2006 | Kunis et al. |
| 2008/0281312 | A1* | 11/2008 | Werneth ............. A61B 18/1206 128/898 |
| 2009/0299355 | A1 | 12/2009 | Bencini et al. |
| 2012/0271135 | A1* | 10/2012 | Burke .................. A61B 5/6858 600/373 |
| 2013/0172715 | A1 | 7/2013 | Just et al. |
| 2013/0289369 | A1 | 10/2013 | Margolis |
| 2014/0052118 | A1 | 2/2014 | Laske |
| 2014/0257069 | A1 | 9/2014 | Eliason et al. |
| 2014/0288552 | A1 | 9/2014 | Kunis et al. |
| 2014/0350553 | A1 | 11/2014 | Okuyama |
| 2015/0119878 | A1 | 4/2015 | Heisel et al. |
| 2015/0223863 | A1 | 8/2015 | Ghosh |
| 2016/0073960 | A1 | 3/2016 | Jung et al. |
| 2016/0338770 | A1 | 11/2016 | Bar-tal et al. |
| 2018/0085064 | A1* | 3/2018 | Auerbach ......... A61M 25/0082 |

FOREIGN PATENT DOCUMENTS

| | | | |
|---|---|---|---|
| JP | 2007507709 | A | 3/2007 |
| JP | 2007537832 | A | 12/2007 |
| JP | 2014014713 | A | 1/2014 |
| JP | 2014512226 | A | 5/2014 |
| JP | 2015089419 | A | 5/2015 |
| JP | 2016007334 | A | 1/2016 |
| JP | 2016507349 | A | 3/2016 |
| JP | 2016515442 | A | 5/2016 |
| JP | 2016104129 | A | 6/2016 |
| WO | 2002045608 | A2 | 6/2002 |
| WO | 2005112813 | A1 | 12/2005 |
| WO | 2005115226 | A2 | 12/2005 |
| WO | 2006115683 | A1 | 11/2006 |
| WO | 2012145072 | A1 | 10/2012 |
| WO | 2012145077 | A1 | 10/2012 |
| WO | 2014137889 | A1 | 9/2014 |
| WO | 2014168987 | A1 | 10/2014 |
| WO | 2013077283 | A1 | 4/2015 |

OTHER PUBLICATIONS

Japanese Notification of Reason for Rejection (Office Action) from related Japanese Application No. 2021-100409 mailed on May 31, 2022, 4 pages including translation.

Chinese Office Action from related Chinese Application No. 201880006464.X mailed on Jun. 28, 2021, 6 pages.

Chinese Search Report from related Chinese Application No. 201880006464.X mailed on Jun. 15, 2021, 3 pages.

European Office Action from related European Application No. 18704326.0 mailed on Mar. 3, 2021, 6 pages.

Japanese Office Action from related Japanese Application No. 2019-537287 mailed on Aug. 18, 2020, 15 pages including translation.

Japanese Notice of Allowance from related Japanese Application No. 2019-537287 mailed on May 18, 2021, 4 pages including translation.

PCT International Search Report and Written Opinion from related PCT International Application No. PCT/US2018/013395 mailed on Apr. 6, 2018, 13 pages.

PCT International Preliminary Report on Patentability from related PCT International Application No. PCT/US2018/013395 mailed on Jul. 16, 2019, 8 pages.

Chinese Office Action from related Chinese Application No. 201880006464.X mailed on Dec. 16, 2021, 14 pages including translation.

Chinese Search Report from related Chinese Application No. 201880006464.X mailed on Dec. 7, 2021, 2 pages.

Chinese Office Action from related Chinese Application No. 201880006464.X mailed on Jun. 28, 2021, 17 pages including translation.

Chinese Search Report from related Chinese Application No. 201880006464.X mailed on Jun. 15, 2021, 6 pages including translation.

* cited by examiner

A - A

B - B

EXPANDABLE MEMBER FOR AN ELECTROPHYSIOLOGY CATHETER

This application is a continuation of U.S. patent application Ser. No. 15/867,657 filed on Jan. 10, 2018, which claims the benefit of priority of U.S. Provisional Patent Application No. 62/445,137, filed Jan. 11, 2017, and these applications are specifically incorporated by reference herein in their entirety.

BACKGROUND

Field

Embodiments are related to electrophysiology (EP) catheters. More particularly, embodiments are related to EP catheters having electrodes mounted on flexible spine assemblies to detect cardiac rhythm disorders.

Background Information

Heart rhythm disorders are common in the United States, and are significant causes of morbidity, lost days from work, and death. Heart rhythm disorders exist in many forms, of which the most complex and difficult to treat are atrial fibrillation, ventricular tachycardia, and ventricular fibrillation. Other rhythm disorders may be easier to treat, but may also be clinically significant, including supraventricular tachycardia, atrial tachycardia, atrial flutter, premature atrial complexes/beats, and premature ventricular complexes/beats. As a result of these cardiac electrical impulse abnormalities, the heart may not be able to expel blood properly, and the blood may pool and clot. A blood clot can move to a peripheral artery or vein, e.g., a neurovessel, and a stroke can result.

Definitive diagnosis of cardiac electrical impulse abnormalities has been performed using electrode-bearing electrophysiology (EP) catheters placed within the heart chambers. EP catheters typically include electrodes positioned along a catheter shaft or an expandable basket to map the electrical activity within a heart chamber. Expandable baskets typically have proximal and distal ends, and include several spines connected at the proximal and distal ends. Each spine can have at least one electrode. Various electrode designs are known, including single curvilinear, lasso-shaped, and multi-branched arrangements. The spines may be expanded to bow radially outward against a wall of the heart chamber, and the electrodes can contact and sense electrical activity within the chamber wall. Typically, the bowed spines are axially oriented and have arc-shaped side profiles between the proximal and distal ends of the expandable basket.

SUMMARY

Existing electrophysiology (EP) catheters do not provide a complete and stable map of electrical activity within a heart chamber. The shape of the heart chambers, e.g., atria, can vary substantially during the beating of the heart. The expandable baskets of existing EP catheters may not provide adequate electrode coverage and/or may not conform to the irregular shape of the atria. More particularly, when expandable baskets of existing EP catheters are deployed, spline elements of the members tend to expand unevenly and do not provide adequate coverage of the target anatomy. Thus, electrodes mounted on the splines may be unevenly distributed within the target anatomy. Uneven distribution of the electrodes can cause incomplete and/or faulty electrograms.

In an embodiment, an expandable member of an EP catheter is provided. The expandable member includes several splines, and each spline has several subsegments extending between a proximal location at a central axis and a distal intersection at the central axis. At least one of the subsegments has a top-down profile extending straight between the central axis and another subsegment. For example, a distal subsegment may extend from the distal intersection to a medial subsegment. The medial subsegment may curve around the central axis toward the proximal location. Accordingly, a distal portion of the expandable member may be radially oriented along a transverse plane, and the medial portion of the expandable member may spiral around the central axis to support the expandable member within a target anatomy.

In an embodiment, the expandable member includes subsegments having straight top-down profiles at both the distal intersection and the proximal location. The distal and proximal subsegments, however, may extend from the central axis to the medial arcuate subsegment in different radial directions. For example, the distal subsegment may extend from the central axis in a first radial direction and the proximal subsegment may extend from the central axis in a second radial direction offset from the first radial direction by an angle in a range of 90-175°. A structural stability of the expandable member and a distribution of electrodes mounted on the spline can be controlled by adjusting the offset angle of the distal and proximal subsegments.

In an embodiment, a distal subsegment of the expandable member includes a concavity that transitions during deployment. For example, the distal intersection of the spline may be an apex of the concavity, and the apex may transition from being a distalmost location on the spline in an undeployed state, to being proximal to a distalmost location on the spline in a deployed state. Accordingly, the distal intersection may be offset from an endocardium after deployment to reduce a risk of tissue damage.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

Various embodiments and aspects of the invention will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present invention.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment. Although the processes depicted in the figures that follow may be described below in terms of some sequential operations, it should be appreciated that some of the operations described can be performed in a different order. Moreover, some operations can be performed in parallel rather than sequentially.

In an aspect, an electrophysiology (EP) catheter having an expandable member to map a target anatomy, e.g., a heart chamber such a ventricle or an atrium, includes a spline having several subsegments extending about a central axis. The spline includes several subsegments that, when viewed in a top-down direction, include straight profiles extending radially from the central axis and arcuate profiles twisting around the central axis. The arcuate profiles may extend continuously from the straight profile such that ends of the arcuate profiles are supported by ends of the straight profiles. Thus, the straight profiles, when viewed from above, may be separated by an angle. The twisting structure of the expandable member can provide structural resilience and stability, and a spacing and distribution of electrodes mounted on the spline may remain uniform when deployed within the atrium. For example, the distribution of the electrodes over an envelope outlined by the opened expandable member may be more or less even based on the angle between the straight profiles. The angle can also control the degree of opening and closing of the expandable member. For example, the amount of opening of the expandable member may be inversely proportional to the angle between the straight profiles. Similarly, the angle between the straight profiles may also affect the ease of opening and closing of the expandable member. For example, the ease of opening of the basket may be inversely proportional to the angle between the straight profiles. Accordingly, the EP catheter can produce stable, complete, and accurate electrograms of the atrial endocardium.

Figure 1:
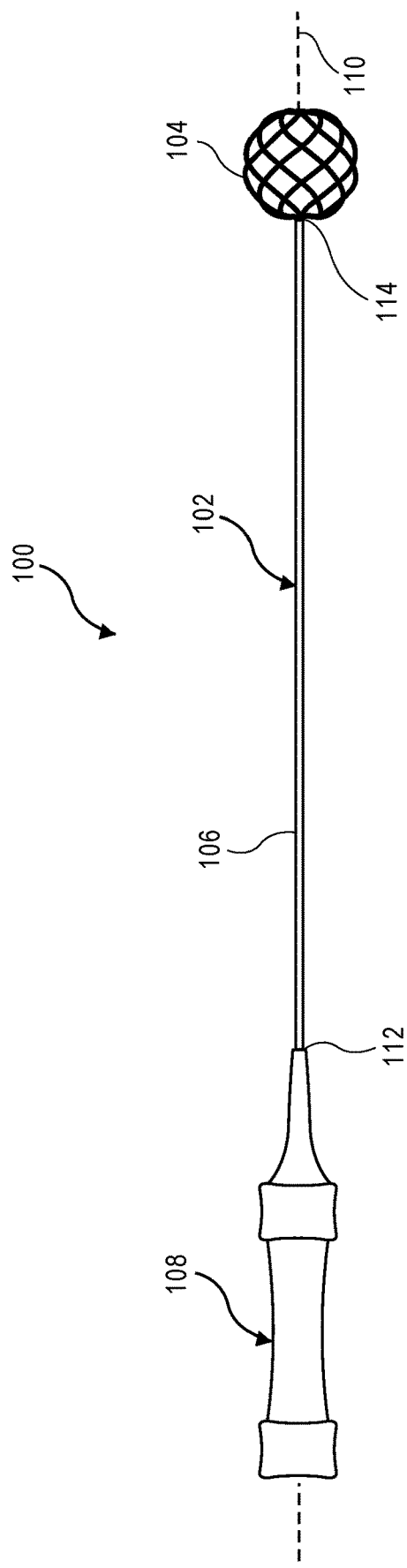
FIG. 1 is a side view of an electrophysiology (EP) catheter system, in accordance with an embodiment.

Referring to FIG. 1, a side view of an electrophysiology catheter system is shown in accordance with an embodiment. An EP catheter system 100 includes an EP catheter 102 having an expandable member 104 connected to a catheter shaft 106. In an embodiment, EP catheter system 100 includes a handle 108 connected to catheter shaft 106. For example, catheter shaft 106 may extend along a central axis 110 between a proximal end 112 and a distal end 114, and handle 108 may be attached to proximal end 112. Handle 108 can provide an interface between a physician and EP catheter 102. Handle 108 may also provide an interface between components of EP catheter system 100 and external components. For example, handle 108 may include an integral connector (not shown) to connect with an electrocardiogram (ECG) data recording system through a data cable.

In an embodiment, handle 108 is connected to expandable member 104 through catheter shaft 106 to allow the physician control movement of expandable member 104 by manipulating handle 108. Expandable member 104 may be joined to a distal end of the catheter shaft 106, e.g., by bonding, potting, or otherwise joining splines of expandable member 104 to catheter shaft 106 at distal end 114.

Figure 2:
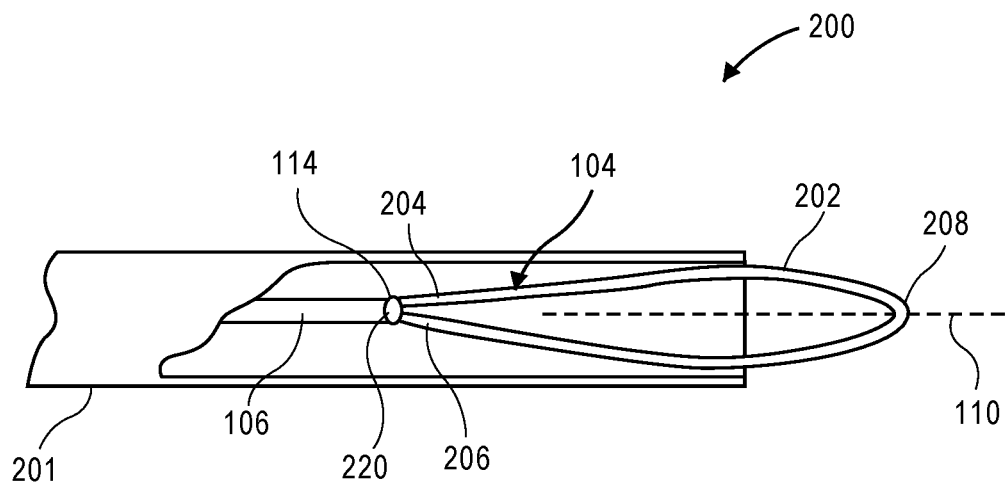
FIG. 2 is a side view of an expandable member in an undeployed state, in accordance with an embodiment.

Referring to FIG. 2, a side view of an expandable member in an undeployed state is shown in accordance with an embodiment. In an undeployed state 200, expandable member 104 may be constrained within an inner lumen of an introducer or guide catheter 201. Introducer or guide catheter 201 may be advanced over expandable member 104 to force the expandable member into a collapsed state. In the collapsed state, expandable member 104 can be advanced into or retracted from the target anatomy.

Expandable member 104 may include one or more splines 202, and thus, a spline 202 may be constrained within the inner lumen. In undeployed state 200, the flexible splines 202 may be arranged in a compressed linear axial orientation. For example, spline 202 may extend between a pair of proximal locations, e.g., a first proximal location 204 and a second proximal location 206 toward a distal tip. The distal tip of spline 202 may be at an intersection between spline 202 and central axis 110. More particularly, a location on spline 202 at the intersection of spline 202 and central axis 110 may be referred to as a distal intersection 208. Thus, in undeployed state 200, spline 202 may extend from first proximal location 204 within catheter shaft 106 to second proximal location 206 within catheter shaft 106 along a path that extends forward to distal intersection 208 and then returns backward to second proximal location 206.

In an embodiment, the proximal locations of spline 202 are connected to catheter shaft 106 at distal end 114. That is, splines 202 may be bonded to catheter shaft 106 by an adhesive or solder joint 220. Joint 220 may secure expandable member 104 to catheter shaft 106 to transmit advancement and retraction forces from handle 108 to expandable member 104 through catheter shaft 106. In an embodiment, when expandable member 104 is in a deployed state (FIG. 3), a joint 220 between expandable member 104 and catheter shaft 106 may be located within 1-2 cm of distal end 114 of catheter shaft 106. More particularly, the joint between spline 202 and catheter shaft 106 may be within an inner lumen of cathether shaft 106 proximal to distal end 114.

Figure 3:
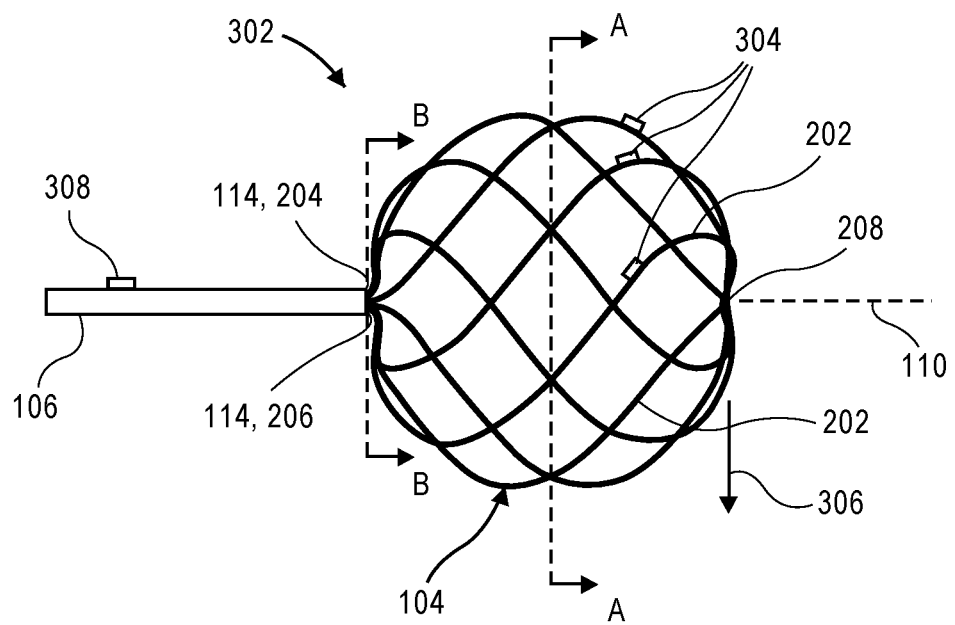
FIG. 3 is a side view of an expandable member in a deployed state, in accordance with an embodiment.

Referring to FIG. 3, a side view of an expandable member in a deployed state is shown in accordance with an embodiment. Expandable member 104 may be advanced from introducer 201 to expand from undeployed state 200 to a deployed state 302. For example, handle 108 may be actuated to advance the pair of proximal locations 204, 206 within the inner lumen of introducer 201 until distal end 114 is distal to a respective distal end of introducer 201. First proximal location 204 and second proximal location 206 on spline 202 may be collocated at distal end 114 of catheter shaft 106. That is, spline 202 may extend unconstrained from first proximal location 204 at distal end 114 to second proximal location 206 at distal end 114.

In deployed state 302, expandable member 104 may have an outer envelope in a shape of a sphere, an ellipsoid, or another bulbous volumetric shape. More particularly, the expanded splines 202 of expandable member 104 may form an outer envelope in deployed state 302, and the outer envelope may approximate a volume of a target anatomy, e.g., a heart atrium. The bulbous volumetric shape of expandable member 104 may have a distal surface that extends transverse to central axis 110. As described below, spline 202 may extend in a transverse direction 306 at distal intersection 208. That is, central axis 110 may be orthogonal to the outer envelope of expandable member 104 at distal intersection 208 in deployed state 302, as defined by splines 202 passing laterally through distal intersection 208 in transverse direction 306. Thus, the outer envelope of deployed expandable member 104 can be a sphere having flattened or concave poles at a proximal and/or distal end.

Each spline 202 of expandable member 104 may include an electrode 304. For example, electrodes 304 may be mounted on splines 202 such that electrodes 304 contact the target anatomy in deployed state 302. In an embodiment, electrodes 304 are on flex circuits that are wrapped over an outer surface of spline 202 to achieve endocardial contact on either side of spline 202, or around half of a circumference of the outer surface of spline 202. Electrodes 304 on splines 202 may be referenced against other electrodes to generate an electrical signal. By way of example, a reference electrode 308 may be mounted on catheter shaft 106. Alternatively, reference electrode 308 may be mounted on a surface of spline 202 that does not contact endocardial tissue during deployment of expandable member 104. For example, reference electrode 308 may be on an inner surface of spline 202. A voltage differential between electrode 304 on a surface of spline 202 facing a target anatomy and reference electrode 308 may be monitored to determine electrical activity in the target anatomy. Accordingly, electrodes on splines 202 may be used to map the atrium.

Figure 4:
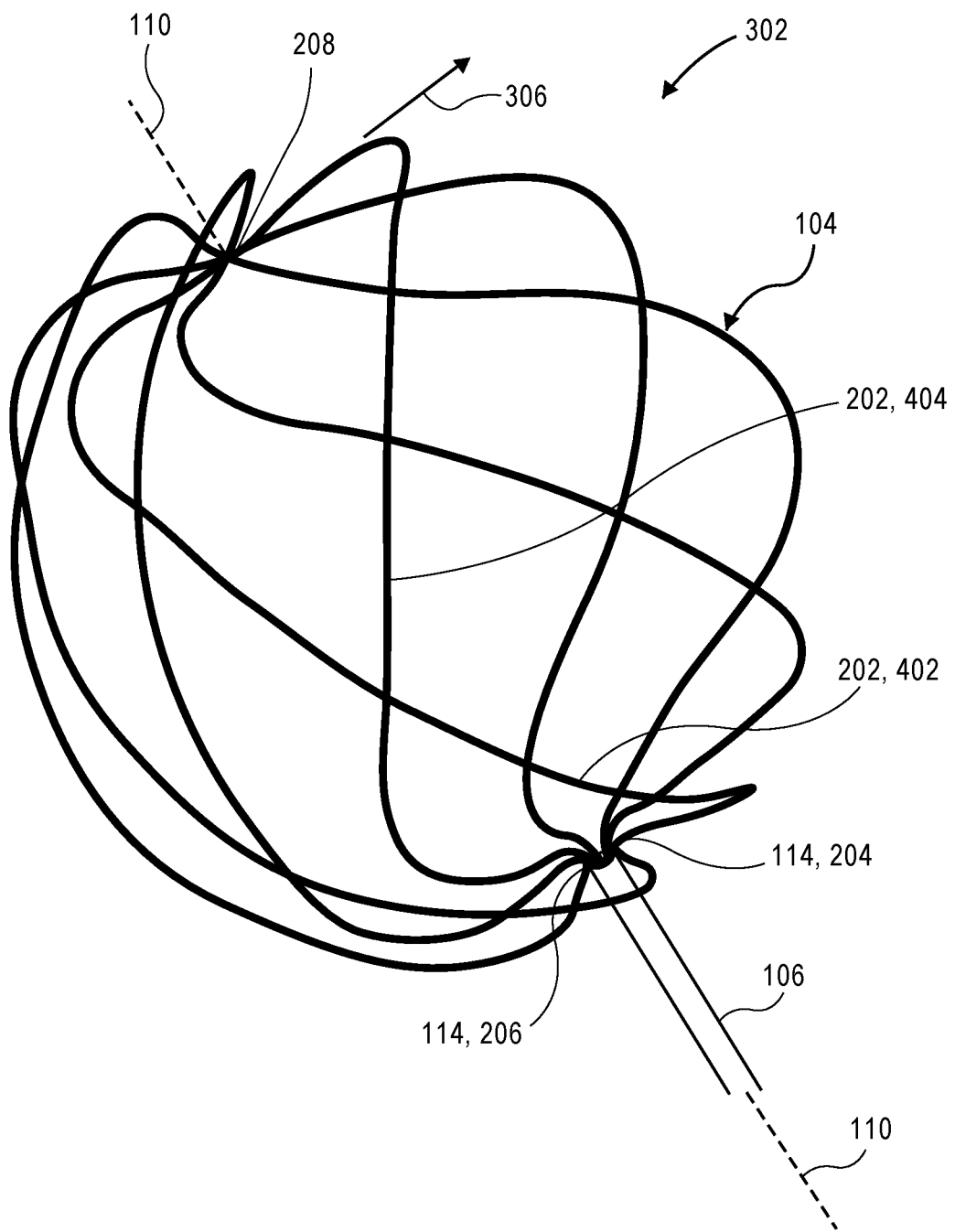
FIG. 4 is a perspective view of an expandable member in a deployed state, in accordance with an embodiment.

Referring to FIG. 4, a perspective view of an expandable member in a deployed state is shown in accordance with an embodiment. Each spline 202 may extend continuously from first proximal location 204 at distal end 114 of catheter shaft 106 to second proximal location 206 at distal end 114. A single spline 202 may extend between the pair of proximal locations, and the single spline 202 may intersect central axis 110 at distal intersection 208. Accordingly, the single spline 202 may extend in transverse direction 306 through central axis 110 to transition from a first spline segment 402 to a second spline segment 404. That is, first spline segment 402 may extend between first proximal location 204 and distal intersection 208, and second spline segment 404 may extend between second proximal location 206 and distal intersection 208.

Figure 6:
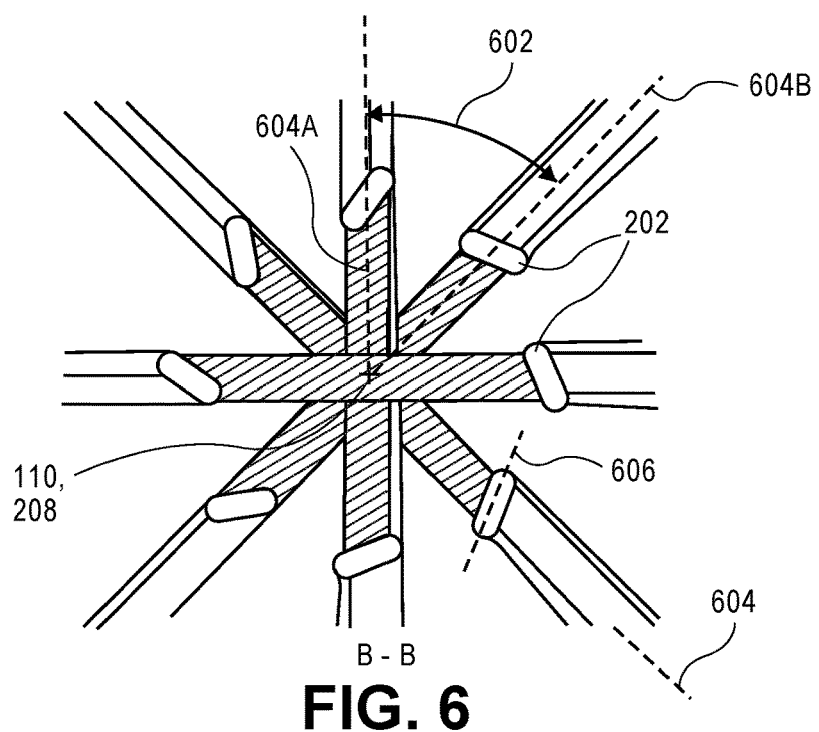
FIG. 6 is a cross-sectional view, taken about line B-B of FIG. 3, of several splines of an expandable member symmetrically arranged about a central axis, in accordance with an embodiment.

The splines 202 of expandable member 104 may overlap each other at distal intersection 208 (FIG. 6). That is, each spline 202 may cross central axis 110 at distal intersection 208 in a respective transverse direction 306. The transverse directions 306 may be within a same transverse plane, however, and the transverse plane may be orthogonal to central axis 110. Accordingly, the overlapping splines 202 may form a transverse envelope surface at distal intersection 208. The transverse envelope surface may be a flattened pole of a spherical envelope.

In an embodiment, the splines 202 are not constrained relative to each other at distal intersection 208, and thus, splines 202 may slide over each other at distal intersection 208. The floating tip and the relative movement of splines 202 at distal intersection 208 can prevent binding or uneven collapse of the struts during retraction of expandable member 104 into an introducer or guide sheath 201. For example, as the splines 202 collapse, they can slide over each other, which may prevent the expandable member 104 from reducing in size in a lopsided or asymmetric manner. Alternatively, a coupling, such as a distal cap, a string or wire winding, or another fastener may bind splines 202 together to constrain relative movement between splines 202 at distal intersection 208.

Figure 5:
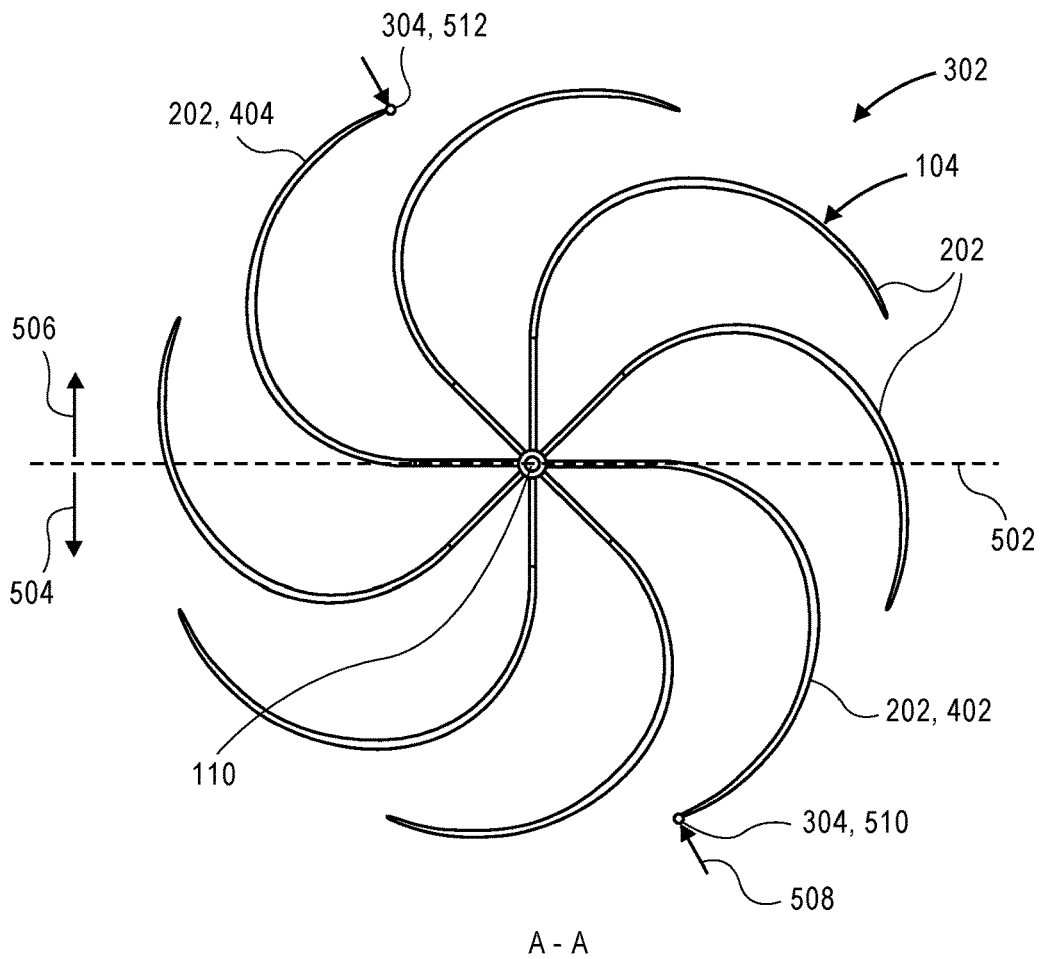
FIG. 5 is a cross-sectional view, taken about line A-A of FIG. 3, of several splines of an expandable member symmetrically arranged about a central axis, in accordance with an embodiment.

Referring to FIG. 5, a cross-sectional view, taken about line A-A of FIG. 3, of several splines of an expandable member symmetrically arranged about a central axis is shown in accordance with an embodiment. In an embodiment, expandable member 104 includes several splines 202 symmetrically disposed about central axis 110. Splines 202 can be symmetrically arranged about central axis 110 when a top-down profile of expandable member 104 has splines 202 bisected by a longitudinal plane 502. Central axis 110 may extend within longitudinal plane 502. Thus, longitudinal plane 502 may be orthogonal to a transverse surface of the outer envelope of expandable member 104 in deployed state 302. A projection of each spline 202 onto a transverse plane orthogonal to the central axis 110 (and longitudinal plane 502) may include first spline segment 402 on a first side 504 of longitudinal plane 502, and second spline segment 404 on a second side 506 of longitudinal plane 502, i.e., on an opposite side of longitudinal plane 502. First spline segment 402 may extend radially outward from central axis 110 on first side 504 of longitudinal plane 502, and second spline segment 404 may extend radially outward from central axis 110 on second side 506 of longitudinal plane 502.

An overall diameter 508 of expandable member 104 may be measured between lateral maxima of expandable member 104. More particularly, a location on first spline segment 402 at a maximum radial distance from central axis 110 may be a first radial limit 510, and a location on second spline segment 404 at a maximum radial distance from central axis 110 may be a second radial limit 512. The radial distance between first radial maximum or limit 510 and second radial maximum or limit 512 may be overall diameter 508. Overall diameter 508 may be adjustable. For example, in deployed state 302, overall diameter 508 may be adjusted by rotating the pair of proximal locations 204, 206 relative to distal intersection 208. More particularly, distal intersection 208 and/or a distal surface of the outer envelope of splines 202 may be pressed against an endocardial surface to fix distal intersection 208 relative to the endocardial surface. Catheter shaft 106 may be rotated, e.g., by rotating handle 108 about central axis 110, and thus the pair of proximal locations 204, 206 coupled to distal end 114 of catheter shaft 106 may rotate about central axis 110 relative to distal intersection 208. Rotation of the pair of proximal locations may twist splines 202 around central axis 110 and cause splines 202 to wind around central axis 110. As splines 202 wind up, overall diameter 508 may decrease. Similarly, when splines 202 are twisted in an opposite direction that cause splines 202 to unwind in an opposite direction about central axis 110, overall diameter 508 may increase. Accordingly, overall diameter 508 may be controlled to cause splines 202 to expand or contract. Expanding splines 202 can move electrodes 304 mounted on the splines outward against the endocardium. For example, electrodes 304 on spline 202 at first radial limit 510 and second radial limit 512 may separate from each other and contact tissue on opposite sides of a heart chamber. Contracting splines 202 can move electrodes 304 inward from the endocardium for retrieval into catheter shaft 106.

Figure 13:
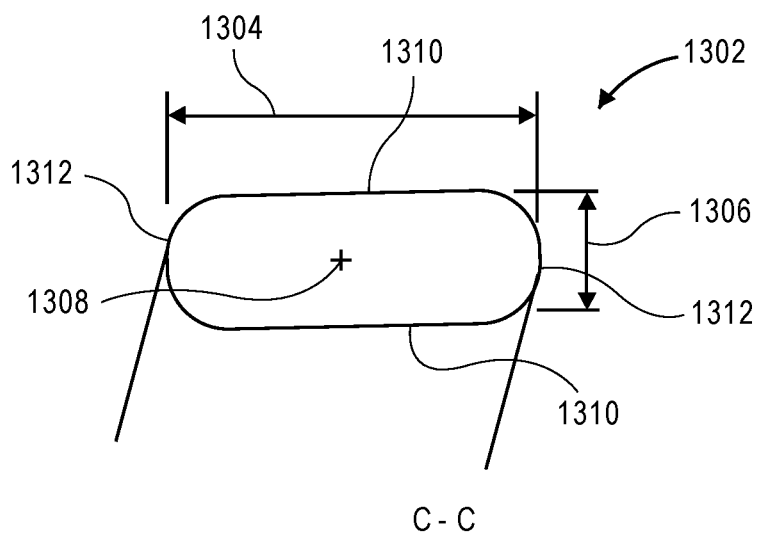
FIG. 13 is a cross-sectional view, taken about line C-C of FIG. 12, of a spline of an expandable member, in accordance with an embodiment.

Referring to FIG. 6, a cross-sectional view, taken about line B-B of FIG. 3, of several splines of an expandable member symmetrically arranged about a central axis is shown in accordance with an embodiment. Each spline 202 may be symmetrically disposed about central axis 110 at distal end 114 of catheter shaft 106. For example, cross-sectional areas of splines 202 at a point where splines 202 enter into the inner lumen of catheter shaft 106 may be arranged circumferentially about central axis 110. The cross-sectional areas around central axis 110 may be spaced apart from each other equally. That is, a peripheral angle 602 separating a radial axis 604 extending from central axis 110 through a first cross-sectional area and a radial axis 604 extending from central axis 110 through a second cross-sectional area may equal 360° divided by the number of spline 202 cross-sectional areas at distal end 114 of catheter shaft 106. More particularly, when eight cross-sectional areas are present at distal end 114, peripheral angle 602 between each adjacent spline may equal 45°. Expandable member 104 may have between 3-24 splines 202, and thus, between 6-48 spline segments and corresponding axes 604 at distal intersection 208, although this is offered by way of example only and not by way of limitation In an embodiment, expandable member 104 is formed from a shape memory material. For example, splines 202 may be drawn Nitinol wire. During a fabrication process, the splines 202 may be heat set in a predetermined configuration. For example, each spline 202 may have a cross-sectional area of a particular shape, e.g., rectoval (FIG. 13). The cross-sectional area may have a width and a height, and the width may be greater than the height. Width may be at least twice height, e.g., width may be 0.015 inch and height may be 0.005 inch. Furthermore, the cross-sectional profile may be tilted relative to central axis 110. For example, a peripheral axis 606 extending parallel to a width of the spline cross-sectional area may not be orthogonal to a corresponding radial axis 604. That is, peripheral axis 606 may be oblique to the corresponding radial axis 604. The tilted profile of spline 202 may resist bending under compressive loads from a surrounding anatomy. Accordingly, cross-sectional areas of splines 202 arranged in a pinwheel fashion may improve stability of the overall structure of expandable member 104.

Each spline 202 of expandable member 104 may twist around central axis 110 between the proximal location at distal end 114 of catheter shaft 106 and distal intersection 208. That is, spline 202 may extend between the proximal location (204 or 206) and distal intersection 208 along a path that has both an axial component and a peripheral component (e.g., circumferentially around central axis 110). FIGS. 7A-7D illustrate top views, which reveal a top-down profile of a single spline 202 of an expandable member 104 exhibiting different degrees of twist about central axis 110 in accordance with several embodiments.

Figure 7A:
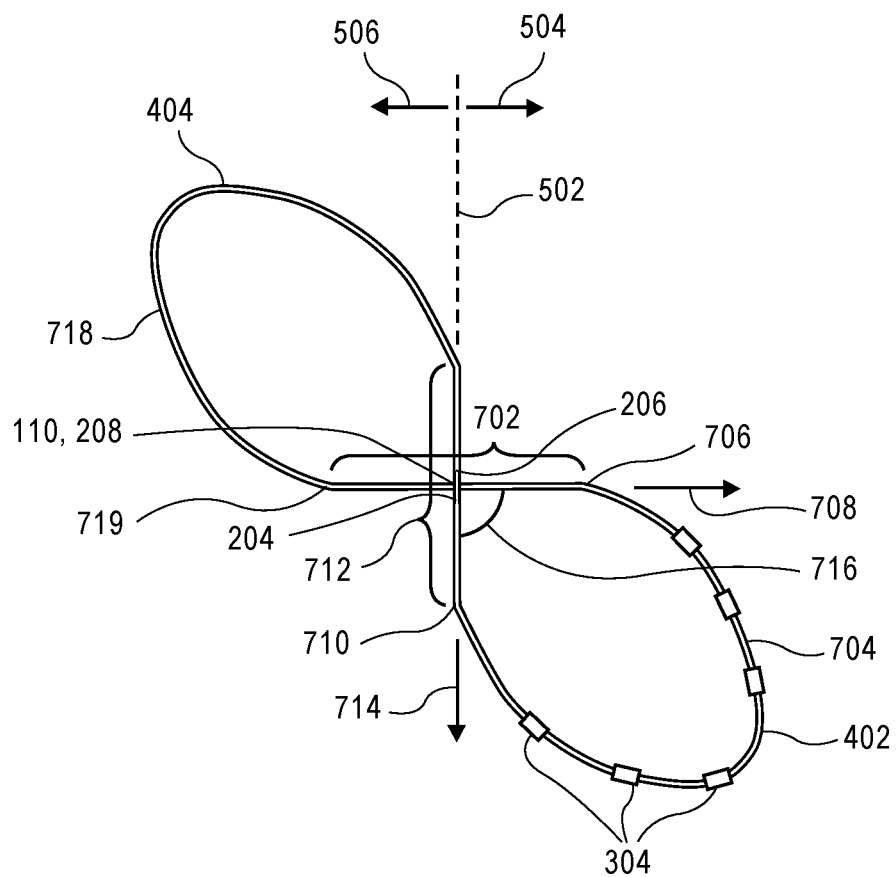
FIGS. 7A-7D are top views, which reveal a top-down profile of a single spline of an expandable member exhibiting different degrees of twist about a central axis, in accordance with several embodiments.

Referring to FIG. 7A, spline 202, which may extend continuously from proximal location 204 to proximal location 206, can be segmented for purposes of description. Spline 202 extending between first proximal location 204 and second proximal location 206 through distal intersection 208 may have a top-down profile resembling a figure-eight. Accordingly, first spline segment 402 extending between first proximal location 204 and distal intersection 208 may have a top-down profile resembling half of a figure-eight. First spline segment 402 may be a circuitous path, such as a loop, extending away from and returning to central axis 110. The top-down profile of first spline segment 402 may be further segmented. For example, the circuitous path of first spline segment 402 may have one or more subsegments exhibiting top-down profiles that are straight and one or more subsegments exhibiting top-down profiles that are curved. The straight and curved profile subsegments may be interconnected to form the continuous circuitous path looping outward and back to central axis 110.

A first subsegment 702 of first spline segment 402 may have a first top-down profile extending straight between central axis 110 and a second subsegment 704 of first spline segment 402. More particularly, first subsegment 702 may extend along a path, which when viewed from above, is linear and in a first radial direction 708. First subsegment 702 may join second subsegment 704 at a distal subsegment end 706 of second subsegment 704. Distal subsegment end 706 may be aligned with central axis 110 in first radial direction 708.

Second subsegment 704 of first spline segment 402 may have a second top-down profile curving between first subsegment 702 and a proximal subsegment end 710. More particularly, second subsegment 704 may extend along a curvilinear path between distal subsegment end 706 and proximal subsegment end 710. The curvilinear path, when viewed from above, may be generally c-shaped. In perspective, however, the curvilinear path may spiral about central axis 110 between a radially outward end of first subsegment 702, and a radially outward end of a third subsegment 712 (FIG. 4).

Third subsegment 712 of first spline segment 402 may have a third top-down profile extending straight between proximal subsegment end 710 of second subsegment 704, and central axis 110. More particularly, third subsegment 712 may extend along a path, which when viewed from above, is linear and in a second radial direction 714. The segment profile of third subsegment 712 may extend along longitudinal plane 502 from proximal subsegment end 710 to central axis 110 continuously within longitudinal plane 502. Accordingly, proximal subsegment end 710 may be aligned with central axis 110 in second radial direction 714.

The spline segments may be joined at distal intersection 208. Accordingly, first spline segment 402 may spiral about central axis 110 on first side 504 of longitudinal plane 502, and second spline segment 404 may spiral about central axis 110 on second side 506 of longitudinal plane 502. Spiraling of the subsegments, however, may be limited to the arcuate portions of spline 202, e.g., second subsegment 704.

Both first spline segment 402 and second spline segment 404 may include portions of first spline subsegment 702 having a top-down profile that extend straight and/or orthogonal to the longitudinal plane 502. In an embodiment, spline 202 includes a fourth subsegment 718 on second side 506 of longitudinal plane 502, opposite from second subsegment 704. Longitudinal plane 502 may be a plane of symmetry dividing second subsegment 704 and fourth subsegment 718. That is, fourth subsegment 718 may form an arc of a half figure-eight profile opposite from the half figure-eight profile of second subsegment 704. Fourth subsegment 718 may spiral about central axis 110 with a different rotational clocking than second subsegment 704. For example, second subsegment 704 may spiral about central axis 110 in a clockwise direction, and fourth subsegment 718 may spiral about central axis 110 in a counterclockwise direction. A form of second subsegment 704 may be geometrically transformed into the form of fourth subsegment 718 by rotating second subsegment 704 about central axis 110 by a rotational angle of 180°.

The top-down profile of first subsegment 702 may extend straight between second subsegment 704 and fourth subsegment 718. For example, fourth subsegment 718 may have a subsegment end 719 mirroring distal subsegment end 706 about longitudinal plane 502. First subsegment 702 may extend between distal subsegment end 706 of second subsegment 704 and subsegment end 719 of fourth subsegment 718.

In an embodiment, an angle 716 between longitudinal planes within which first subsegment 702 and third subsegment 712 respectively extend determines a degree of twist of first spline segment 402 about central axis 110. The top-down profile of first subsegment 702 and the top-down profile of third subsegment 712 may extend in respective radial directions from central axis 110, and the radial directions may be separated by angle 716. By way of example, angle 716 may be in a range of 70-200°. Still referring to FIG. 7A, angle 716 may be nominally 90°, and may vary within manufacturing tolerances of +/−20°. Accordingly, first spline segment 402 may extend from first proximal location 204 to distal intersection 208 over a quarter twist about central axis 110. Second segment 404 may be symmetric relative to first segment 402, and thus, a twist angle of second segment 404 may be similarly determined. The term symmetric here describes a rotation symmetry between second segment 404 and first segment 402. That is, the form of first segment 402 may be rotated about central axis 110 over an angle of 180° to coincide with the form of second segment 404.

It will be appreciated that the twist of the splines about central axis 110 may be defined or modified in manners other than adjusting angle 716. For example, angle 716 may be 90° as defined above, however, the transition from first subsegment 702 or third subsegment 712 to second subsegment 704 may differ from the example illustrated in FIG. 7A. That is, the transition may not be smooth, but may instead be angled. Furthermore, the profile of second subsegment may not follow a continuous arc between first subsegment 702 and third subsegment 712, but may instead undulate or otherwise advance along the envelope defined by the expandable member 104. In short, the embodiments illustrated in FIG. 7A-7D are illustrative and are not be considered limiting of other spline profiles that may be contemplated by one skilled in the art.

Figure 7B:
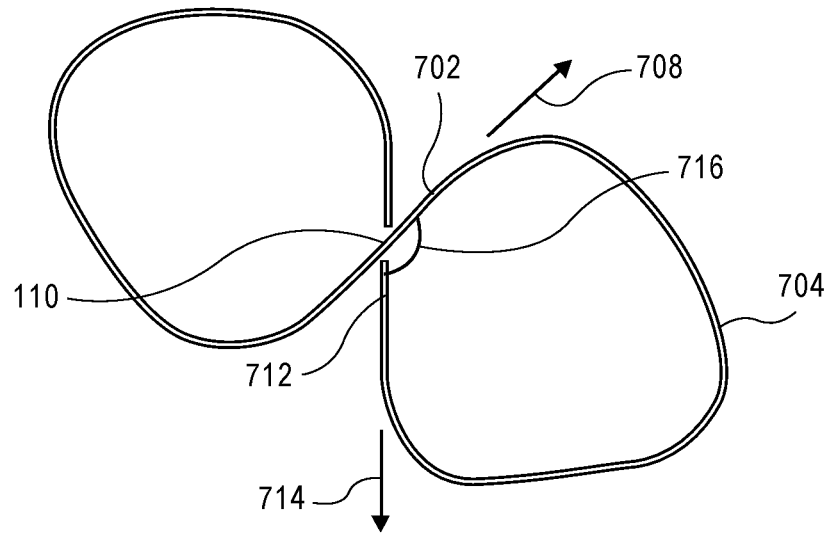

The twist angle of the spline segments may be different in other embodiments. Referring to FIG. 7B, first subsegment 702 may extend in first radial direction 708 away from central axis 110, and third subsegment 712 may extend in second radial direction 714 away from central axis 110. The longitudinal planes within which first subsegment 702 and third subsegment 712 are contained (and within which central axis 110 is contained) may be spaced apart by angle 716 of about 135°. For example, angle 716 between the top-down profiles of first subsegment 702 and third subsegment 712 may be in a range of 115-155°.

Figure 7C:
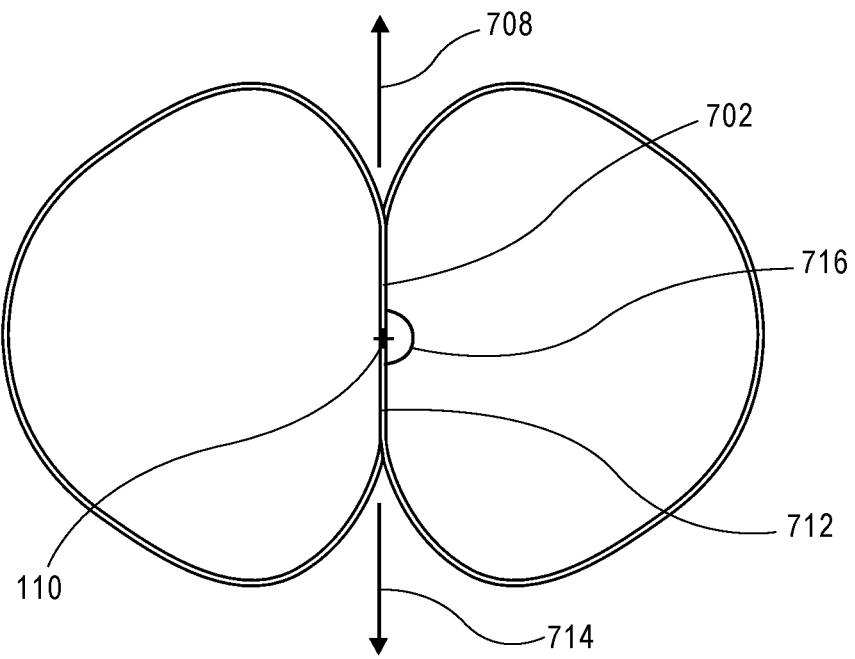

Referring to FIG. 7C, first subsegment 702 may extend in first radial direction 708 away from central axis 110, and third subsegment 712 may extend in second radial direction 714 away from central axis 110. The radial directions may be opposite directions from one another. That is, the longitudinal planes within which first subsegment 702 and third subsegment 712 are contained may be spaced apart by angle 716 of about 180°. For example, angle 716 between the top-down profiles of first subsegment 702 and third subsegment 712 may be in a range of 160-200°.

The degree of twist of spline segments about central axis 110 may determine different levels of chamber wall apposition of electrodes 304 and/or structural stability of expandable member 104. As described above, expandable member 104 can include one or more electrodes 304 mounted on an outward facing surface of spline 202. For example, electrodes 304 may be mounted on second subsegment 704 of spline 202 along the curvilinear path radially outward from central axis 110. In an embodiment, angle 716 determines a pitch angle of spline 202 relative to a transverse plane, and accordingly, angle 716 determines a density of electrodes 304 in contact with an endocardium. Increasing angle 716 may increase an amount of the outer surface area of spline 202 that contacts the endocardium, and thus, may increase a density of electrode contact. For example, a distance between the proximal location and the distal location of spline 202 may be longer for larger angles 716, which can result in more electrodes 304 in contact with endocardium. Accordingly, angle 716 may be tuned to achieve an amount of apposition between electrodes 304 on spline 202 and the endocardium. Angle 716 may also affect a resilience of expandable member 104. For example, smaller angles 716 may cause splines 202 to be more axially aligned than circumferentially aligned relative to the heart chamber, and thus, smaller angles 716 may create stiffer and more robust structures. Accordingly, angle 716 may be tuned to achieve a balance between electrode apposition and structural rigidity.

Figure 7D:
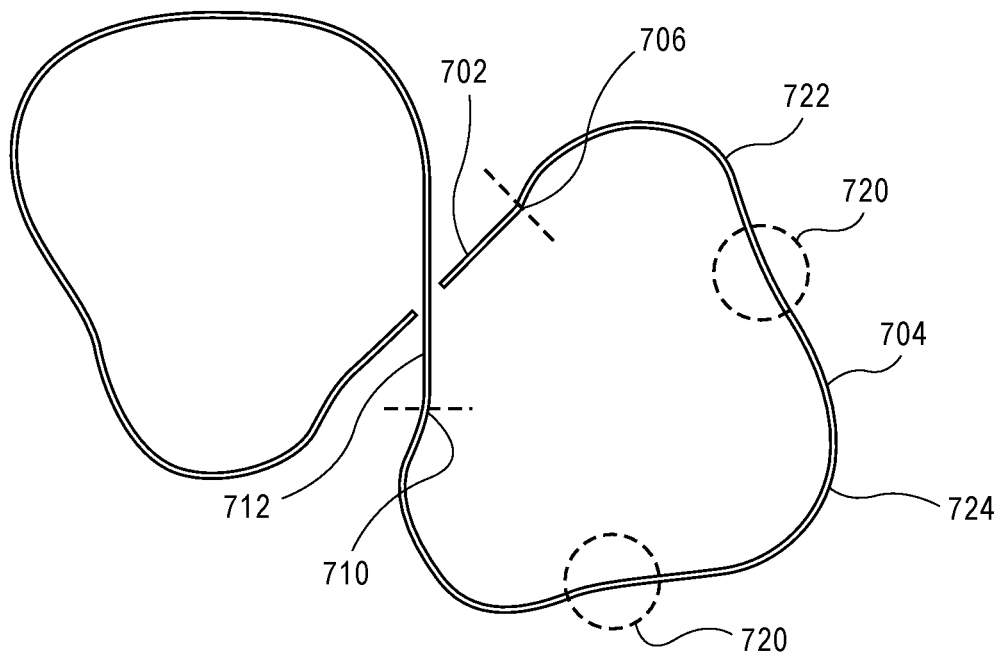

Referring to FIG. 7D, structural rigidity may be further tuned by introducing local bends in the subsegments of spline 202. For example, second subsegment 704, which extends between distal subsegment end 706 and proximal subsegment end 710, may include one or more undulations 720. Undulations 720 may be localized bends or curvatures having different radii than surrounding portions of second subsegment 704. For example, undulation 720 may be located along second subsegment 704 between a first subsegment portion 722 and a second subsegment portion 724. First subsegment portion 722 and second subsegment portion 724 may have radii measured from longitudinal axes on a first side of second subsegment 704, e.g., within the loop circumscribed by the top-down profile of second subsegment 704. Undulation 720 may have a radius measured from a longitudinal axis on a second side of second subsegment 704, e.g., outside of the loop circumscribed by the top-down profile of second subsegment 704. Thus, undulation 720 may have an inflection point at which first subsegment portion 722 transitions into second subsegment portion 724. Undulations 720 may be included at various locations along second subsegment 704 to create different rates of load bearing throughout spline 202. Spline 202 may therefore resist forces applied by the endocardium in different directions and be less susceptible to crushing. That is, undulations 720 may increase a structural stability of expandable member 104.

Figure 8:
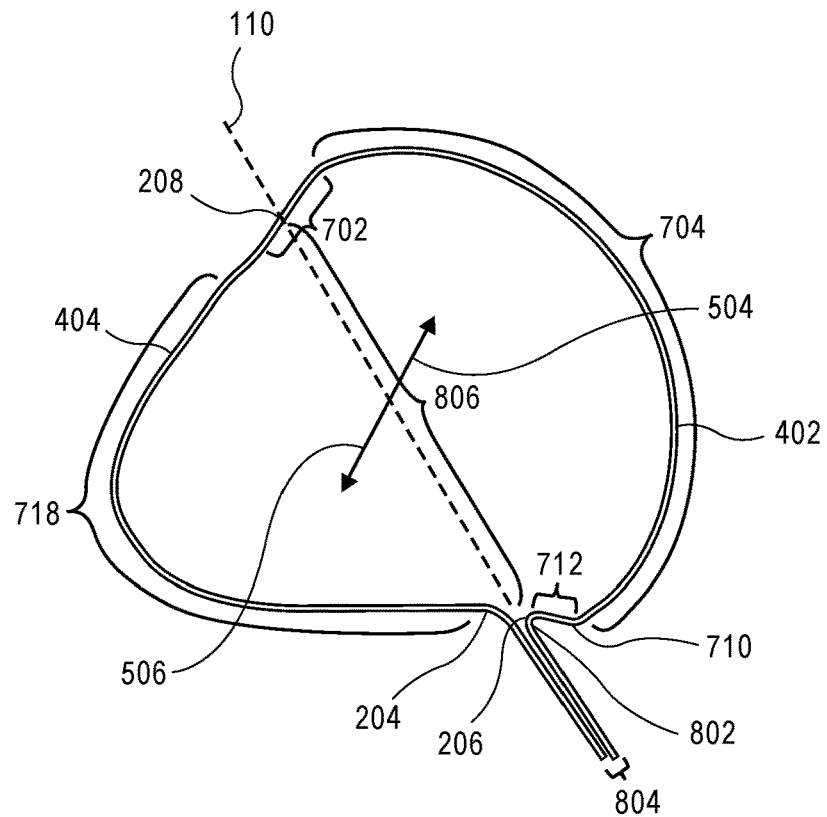
FIG. 8 is a perspective view of a spline of an expandable member exhibiting a twist about a central axis, in accordance with an embodiment.

Referring to FIG. 8, a perspective view of a spline of an expandable member exhibiting a twist about a central axis is shown in accordance with an embodiment. The perspective view shows spline 202 in deployed state 302, and having spline segments that twist about central axis 110 over a 90° angle 716. As described above, angle 716 may vary, and thus, the following description may be applicable to spline twisting of various degrees. In an embodiment, first subsegment 702 intersects central axis 110 at distal intersection 208. First subsegment 702 may extend through central axis 110 from second subsegment 704 on first side 504 of longitudinal plane 502 to fourth subsegment 718 on second side 506 of longitudinal plane 502. Similarly, first spline segment 402 and second spline segment 404 may meet central axis 110 at a proximal intersection 802, e.g., at proximal locations of expandable member 104. For example, third subsegment 712 of first spline segment 402 may extend radially inward toward central axis 110 from proximal subsegment end 710 to proximal intersection 802. Third subsegment 712 may be considered to intersect central axis 110 at proximal intersection 802 even when third subsegment 712 and central axis 110 do not actually coincide at a point. More particularly, in an embodiment, spline subsegments running through the inner lumen of catheter shaft 106 may be symmetrically disposed about central axis 110 and separated from each other by a spline gap 804. That is, each spline subsegment within the inner lumen may be separated from an adjacent spline subsegment by an equal angle about central axis 110. Spline gap 804 may be small, e.g., on an order of one millimeter, and thus the spline subsegments may never actually coincide with central axis 110 that runs between them. Nonetheless, for the purposes of understanding, spline 202 may be considered as intersecting central axis 110 at the pair of proximal locations and/or at distal end 114 of catheter shaft 106.

Similar to the lateral separation between proximal locations 204, 206 of spline 202, the pair of proximal locations may be axially separated from a distal location of spline 202. More particularly, proximal intersection 802 may be separated from distal intersection 208 along central axis 110. The space between distal intersection 208 and proximal intersection 802 may be referred to as an axial gap 806. Axial gap 806 may be distinguished from, e.g., a central shaft interconnecting a proximal portion and a distal portion of an expandable basket. More particularly, distal intersection 208 and proximal intersection 802 may be separated by a space and allowed to float relative to each other. Distal intersection 208 and proximal intersection 802 of spline 202 may be connected only by the spline segments twisting outward and around central axis 110. A lack of a central shaft can allow the tip of expandable member 104 at distal intersection 208 to float freely relative to a base of expandable member 104 attached to catheter shaft 106 at proximal intersection 802. The floating tip may therefore adjust to anatomical variations more readily, and expandable member 104 may resultantly include greater structural resilience than an expandable basket having a central shaft throughout the basket length.

Figure 9:
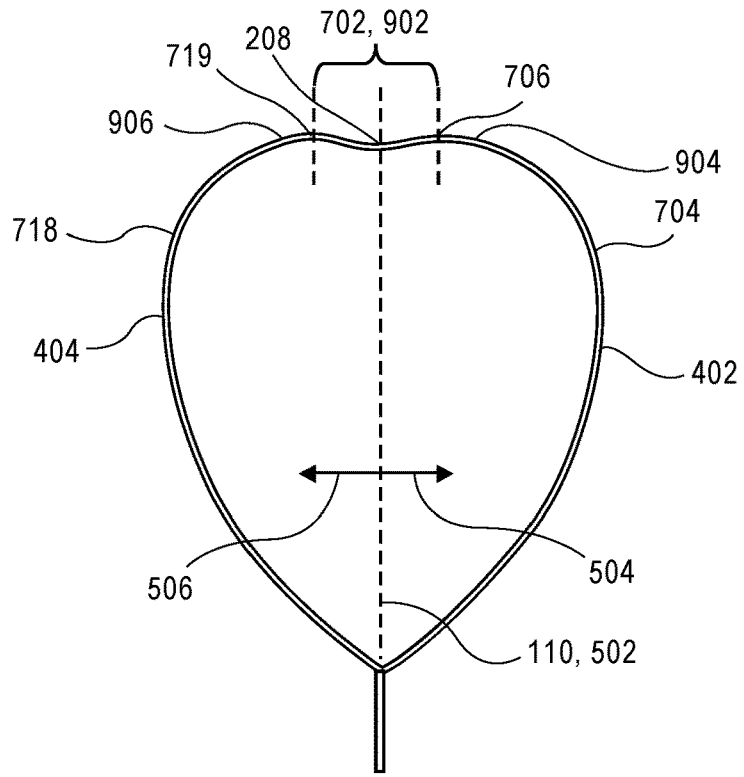
FIG. 9 is a side view of a spline of an expandable member exhibiting a twist about a central axis, in accordance with an embodiment.

Referring to FIG. 9, a side view of a spline of an expandable member exhibiting a twist about a central axis is shown in accordance with an embodiment. The side view is for a spline having a spline segment twisting 90° about central axis 110, but the illustrated aspects are applicable to the other spline configurations described above. The side view shows that first subsegment 702 may have a side profile that is not straight between second subsegment 704 and fourth subsegment 718. First subsegment 702 may be bowed. First subsegment 702 of spline 202 may be an arcuate spline segment 902 having a side profile that curves within a longitudinal plane containing central axis 110. It will be appreciated that arcuate spline segment 902 may extend from distal subsegment end 706 of second subsegment 704 through central axis 110 to subsegment end 719 of fourth subsegment 718. Thus, a central portion of arcuate spline segment 902 may be at a different axial height along central axis 110 than the radially outward ends of arcuate spline segment 902.

In an embodiment, first spline segment 402 has a first distalmost location 904 on first side 504 of longitudinal plane 502, and second spline segment 404 has a second distalmost location 906 on second side 506 of longitudinal plane 502. First distalmost location 904 may or may not be at the distal subsegment end 719, and second distalmost location 906 may or may not be at subsegment end 719. That is, the distalmost locations are at the most distal points on spline 202 regardless of whether the points are on a particular subsegment based on the subsegment profile definitions described above.

Figure 10:
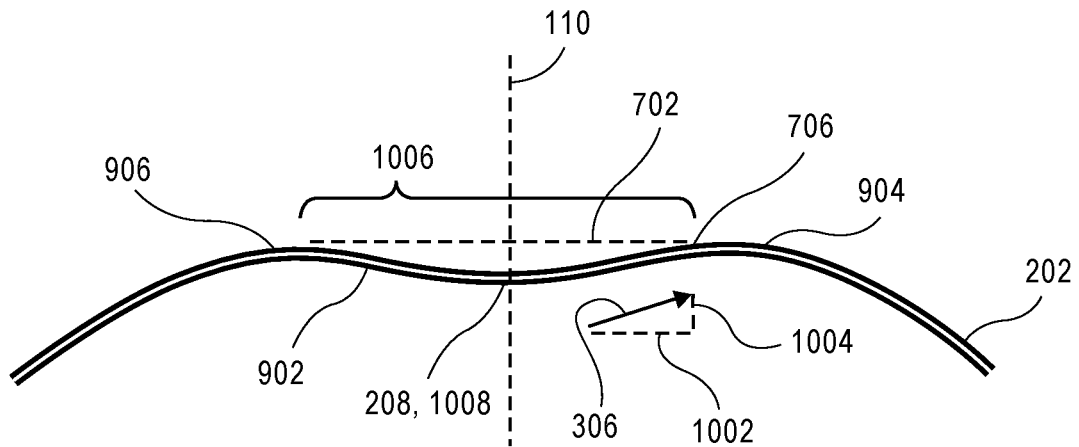
FIG. 10 is a side view, which reveals a side profile of a distal portion of an expanded spline of an expandable member, in accordance with an embodiment.

Referring to FIG. 10, a side view, which reveals a side profile of a distal portion of an expanded spline of an expandable member is shown in accordance with an embodiment. The distalmost locations of spline 202 may be distal to distal intersection 208 in deployed state 302. For example, arcuate spline segment 902 may extend from first distalmost location 904 to second distalmost location 906 through distal intersection 208, and distal intersection 208 may be nearer to catheter shaft 106 than the distalmost locations. Thus, first subsegment 702 may have a bowed side profile. Alternatively, distalmost locations and distal intersection 208 may be arranged at a same axial distance from catheter shaft 106 in deployed state 302. For example, as shown by the dashed line in FIG. 10, first subsegment 702 may have a side profile extending straight between first distalmost location 904 and second distalmost location 906. Accordingly, the radially oriented subsegment may extend within a transverse plane containing both distal intersection 208 and the distalmost locations 904, 906. In deployed state 302 therefore, distal intersection 208 may be axially aligned with or proximal to distal subsegment end 719.

Whether first subsegment 702 has a straight or arcuate side profile, spline 202 extends in transverse direction 306 from central axis 110 to the distalmost locations 904, 906. Transverse direction 306, however, may have a radial component 1002 and/or an axial component 1004. Radial component 1002 may be a component of transverse direction 306 orthogonal to central axis 110 at distal intersection 208. More particularly, a line drawn tangent to first subsegment 702 at distal intersection 208 may have a component that extends radially away from central axis 110. Axial component 1004, on the other hand, may be a component of transverse direction 306 parallel to central axis 110 at distal intersection 208. More particularly, the line drawn tangent to first subsegment 702 at distal intersection 208 may have a component that extends along central axis 110. When the line drawn tangent to first subsegment 702 at distal intersection 208 includes both radial component 1002 and axial component 1004, transverse direction 306 is oblique to central axis 110. On the other hand, when the line drawn tangent to first subsegment 702 at distal intersection 208 extends in transverse direction 306 having only radial component 1002, transverse direction 306 is orthogonal to central axis 110, i.e., radiates from central axis 110.

Spline 202 may have a concavity 1006 in one or both of deployed state 302 or undeployed state 200. For example, arcuate spline segment 902 having distalmost locations 904, 906 distal to distal intersection 208 may have concavity 1006 that bows in an axial direction. Concavity 1006 may include an apex 1008 on central axis 110 at distal intersection 208. Apex 1008 may be proximal to distalmost locations 904, 906 when concavity 1006 is concave upward (FIG. 10). Thus, in an embodiment, concavity 1006 is concave upward in deployed state 302.

A concave upward concavity 1006 can provide an atraumatic tip to expandable member 104. That is, since distalmost locations 904, 906 are axially offset from distal intersection 208, the distal intersection 208 may be offset from endocardial tissue in deployed state 302. Furthermore, arcuate spline segment 902 can be flexible such that the distal portion of expandable member 104 is resilient when pressed forward against tissue. The resilience can reduce a likelihood of causing tissue damage during manipulation of the expandable member 104, and thus, arcuate spline segment 902 provides an atraumatic tip for expandable member 104 in deployed state 302.

Arcuate spline segment 902 can provide a spring force acting in a transverse direction on second subsegment 704 and fourth subsegment 718. For example, subsegment ends 706, 719 may connect to respective ends of arcuate spline segment 902, and the respective ends may resist radial forces applied to subsegments 704, 718 by a surrounding endocardial tissue. Accordingly, arcuate spline segment 902 can increase a radial stiffness of expandable member 104 in deployed state 302. The radial stiffness of expandable member 104 having arcuate spline segment 902 with a curved side profile may be greater than a radial stiffness of expandable member 104 having first subsegment 702 with a straight side profile, as indicated by the dashed line.

Expandable member 104 may also include a concavity near proximal ends 204, 206 (not shown). For example, third subsegment 712 may curve in a distal direction from proximal subsegment end 710 to proximal end 206. That is proximal subsegment end 710 may be more proximal than proximal end 206. Accordingly, a proximal portion of expandable member 104 may have a concave downward configuration forming a dimple at the proximal region of the envelope formed by expandable member 104.

Figure 11:
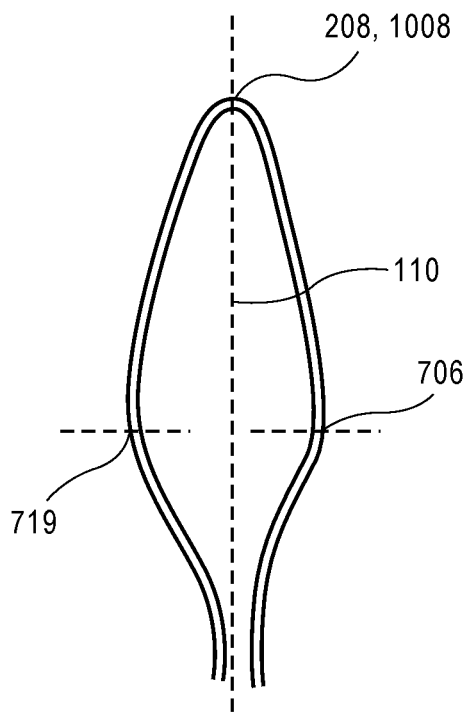
FIG. 11 is a side view of a distal portion of an unexpanded spline of an expandable member, in accordance with an embodiment.

Referring to FIG. 11, a side view of a distal portion of an unexpanded spline of an expandable member is shown in accordance with an embodiment. Apex 1008 may be distal to subsegment ends 706, 719 when concavity 1006 is concave downward. More particularly, apex 1008 at distal intersection 208 along central axis 110 may be a distalmost location of spline 202 when spline 202 is constrained within, or in the process of deploying from, introducer 201. Distal intersection 208 may therefore be distal to distal subsegment end 706 and/or subsegment end 719 in undeployed state 200. Accordingly, first subsegment 702 may be bowed with concavity 1006 being concave downward in undeployed state 200.

Figure 12:
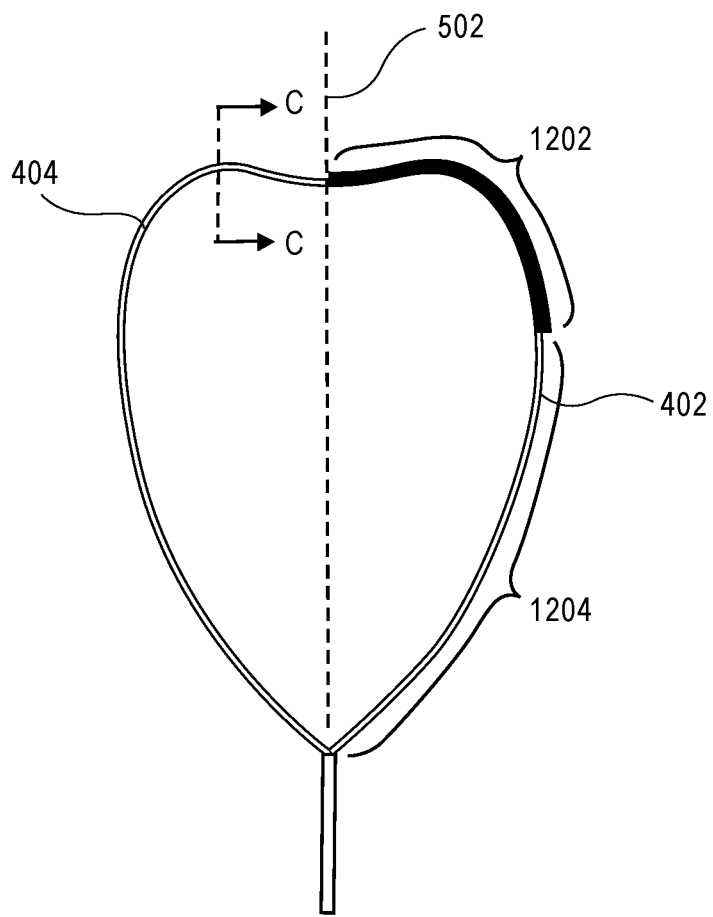
FIG. 12 is a side view of a spline of an expandable member having portions of varying radiopacity, in accordance with an embodiment.

Referring to FIG. 12, a side view of a spline of an expandable member having portions of varying radiopacity is shown in accordance with an embodiment. In addition to defining segments and subsegments of spline 202 based on top-down and side profiles, spline portions may be defined according to relative radiopacity. For example, a first portion 1202 of first spline segment 402 may have a first radiopacity, and a second portion 1204 of first spline segment 402 may have a second radiopacity. The radiopacity of first portion 1202 may be different than the radiopacity of second portion 1204. For example, first portion 1202 may be more radiopaque than second portion 1204 (as indicated by the varying line thickness). The difference in radiopacity between first portion 1202 and second portion 1204 can indicate to a physician a relative placement of the portions within a target anatomy. For example, when first portion 1202 is distal to second portion 1204, a physician may recognize first portion 1202 as a darker image on a fluoroscope, and may therefore determine a relative placement of expandable member 104 within the target anatomy.

In an embodiment, portions of differing radiopacity may correspond to the subsegments described above. For example, second subsegment 704 and/or fourth subsegment 718 may have equivalent radiopacities. By contrast, the radiopacities of second subsegment 704 and/or fourth subsegment 718 may differ from a radiopacity of first subsegment 702 or third subsegment 712. As a result, both the subsegment profiles and subsegment densities may provide to an observer indications of an orientation of expandable member 104 within the target anatomy.

Radiopacity of the spline portions may be tuned. For example, metallic radiomarkers may be added to spline 202 to vary radiopacity. A material, size, or density of spline 202 may also be varied to achieve a desired radiopacity. By way of example, first portion 1202 may be doped with radiopaque filler to increase a respective radiopacity relative to second portion 1204. Other manners of tuning radiopacity are known in the art.

Referring to FIG. 13, a cross-sectional view, taken about line C-C of FIG. 12, of a spline of an expandable member is shown in accordance with an embodiment. Spline 202 may have a cross-sectional profile 1302 of a given shape. As described above, cross-sectional profile 1302 may have a width 1304 and a height 1306. Width 1304 and height 1306 may be equal, e.g., in the case of a square or a circular cross-sectional profile 1302. Alternatively, width 1304 may be greater than height 1306, e.g., in the case of an elliptical cross-sectional profile 1302. Cross-sectional area may include at least one flat side facing outward toward an endocardium in deployed state 302. For example, cross-sectional area may be an oval, triangle, flattened circle, or rectangle having a flattened surface facing outward. Cross-sectional profile 1302 may vary over a length of spline 202. For example, cross-sectional profile 1302 may have a first orientation relative to an axial axis 1308 of spline 202, as illustrated in FIG. 13, and at a different location along spline 202 cross-sectional profile 1302 may have a different second rotational orientation relative to axial axis 1308. Width 1304 may be horizontal in the first orientation, and vertical in the second orientation, relative to axial axis 1308. Accordingly, cross-sectional profile 1302 may revolve about axial axis 1308 along the length of spline 202.

In an embodiment, the orientation of cross-sectional profile 1302 relative to axial axis 1308 may vary along the length of spline 202 to achieve a predetermined relationship between portions of spline 202 and a surrounding environment. For example, cross-sectional profile 1302 may have an outward facing flat surface, and cross-sectional profile 1302 may twist about axial axis 1308 to face the outward facing flat surface toward endocardial tissue when expandable member 104 is in deployed state 302. In an embodiment, a radial vector radiating from a midpoint on central axis 110 half of a distance between the proximal location 114 and the distal intersection 208 passes orthogonal to the axial axis 110 and the outward surface. Accordingly, the outward facing flat surface faces radially outward from the midpoint, which may be located near a central point of an atrium in deployed state 302. Electrodes 304 may be mounted on the outward facing flat surface of cross-sectional profile 1302, and thus, electrodes 304 may be in contact with the endocardial tissue to sense electrical activity in deployed state 302.

In an embodiment, cross-sectional profile 1302 of spline 202 is rectoval. The term rectoval is used to describe a profile having a generally rectangular shape with rounded corners. As such, cross-sectional profile 1302 may include flat outer surfaces 1310 on opposite sides of axial axis 1308, and the outer surfaces 1310 may be connected by sidewalls 1312 extending between the outer surfaces 1310. Sidewalls 1312 may have radii and/or may include chamfers or fillets at corners where sidewalls 1312 transition into outer surfaces 1310. The rectoval, or ribbon-shaped, cross-sectional area may allow an electrode 304 to reside on an outward facing (tissue contacting) surface of spline 202. The shape may provide stability of splines 202 when contacting endocardial tissue. Such stability can prevent crushing or collapse of expandable member 104.

Figure 14:
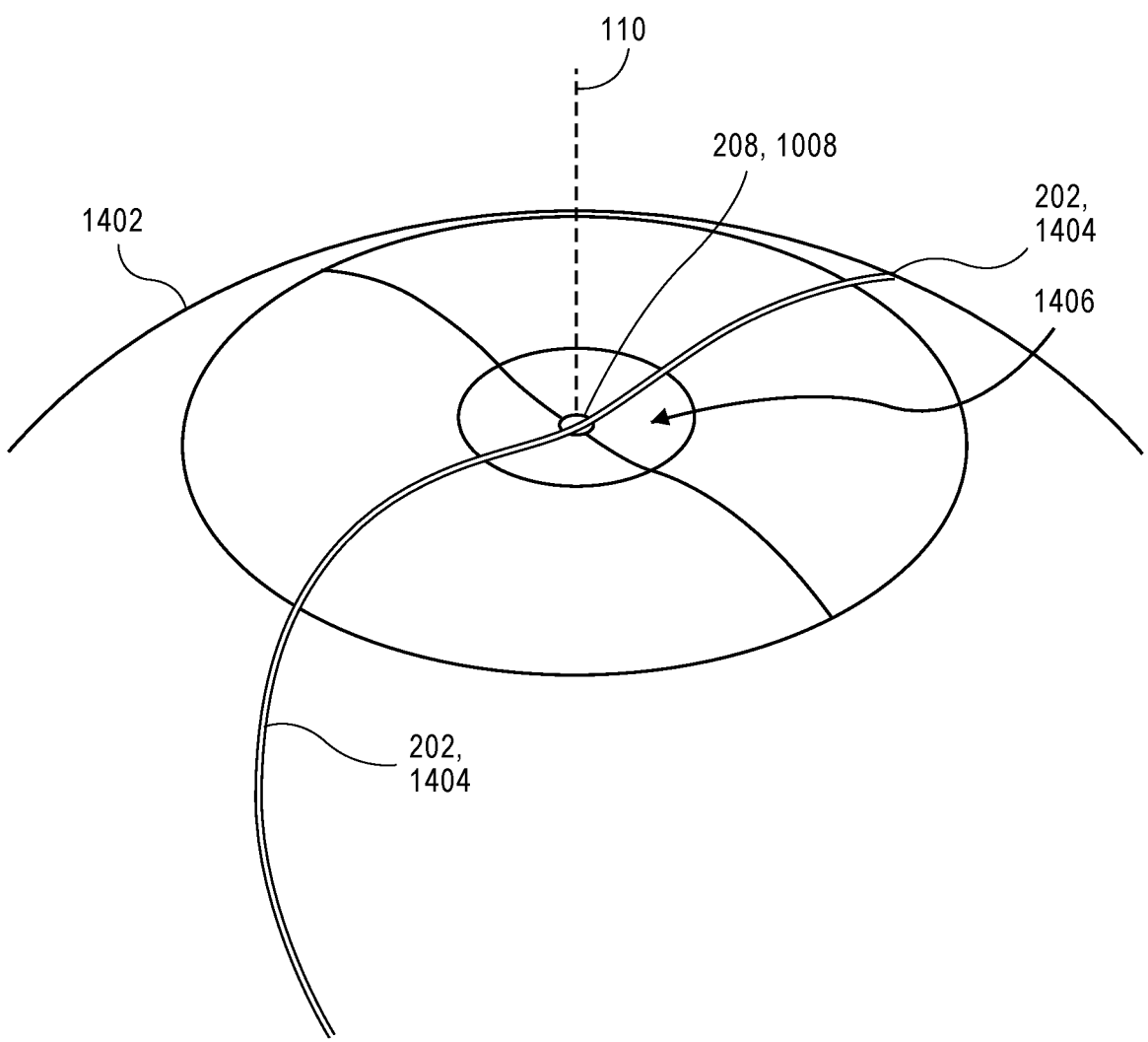
FIG. 14 is a perspective view of an outer envelope of an expandable member, in accordance with an embodiment.

Referring to FIG. 14, a perspective view of an outer envelope of an expandable member is shown in accordance with an embodiment. Examples of several splines 202 are shown to convey that an outer envelope 1402 is a geometrical form representing a three-dimensional surface corresponding to a revolved surface of spline 1404 rotated about central axis 110 by 360°. That is, outer envelope 1402 corresponds to a revolved surface formed by revolving spline 1404, however, a similar surface with a slightly different profile could be formed by revolving another example spline 202. In either case, outer envelope 1402 can include a dimple 1406 around distal intersection 208. Dimple 1406 corresponds to concavity 1006 of the side profile of spline 202 (FIG. 10). As described above, a similar dimple may exist at a proximal region of the envelope (not shown). Dimple 1406 can include a curved depression in a surface that transitions smoothly from a generally spherical outer surface of expandable member 104 to an indentation near apex 1008. The transition area between the spherical outer surface and the distal concavity provides an atraumatic outer envelope for expandable member 104.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. An expandable member, comprising:
a spline extending continuously between a pair of proximal locations on a catheter shaft and intersecting at a central axis, the spline including a first subsegment, a second subsegment, and a flex circuit, wherein the first subsegment, when viewed in an axial direction along the central axis, extends along a linear path in a radial direction between a distal intersection at the central axis and a distal subsegment end of the second subsegment, wherein the second subsegment has a uniform cross-sectional area and, when viewed in the axial direction along the central axis, undulates along a curvilinear path having a plurality of localized bends bending in different directions between the distal subsegment end and a proximal subsegment end of the second subsegment, and wherein the flex circuit includes a plurality of electrodes and the flex circuit is wrapped around a circumference of an outer surface of the spline.

2. The expandable member of claim 1, wherein the second subsegment undulates about the central axis along the curvilinear path.

3. The expandable member of claim 2, wherein the second subsegment undulates continuously.

4. The expandable member of claim 1, wherein the spline includes a third subsegment, and wherein a third top-down profile of the third subsegment viewed in the axial direction along the central axis is straight between the proximal subsegment end of the second subsegment and the central axis.

5. The expandable member of claim 1 further comprising a reference electrode mounted on a non-tissue-contacting surface of the expandable member.

6. The expandable member of claim 1, wherein the expandable member has a spherical envelope including one or more of a concave pole or a flattened pole.

7. The expandable member of claim 1, wherein the distal intersection is axially aligned with the distal subsegment end.

8. The expandable member of claim 1, wherein the distal intersection is proximal to the distal subsegment end.

9. The expandable member of claim 1, wherein a first portion of the spline has a different radiopacity than a second portion of the spline.

10. An electrophysiology catheter, comprising:
a catheter shaft extending along a central axis between a proximal end and a distal end; and
an expandable member mounted on the distal end, the expandable member including a spline extending continuously between a pair of proximal locations on the catheter shaft and intersecting at the central axis, the spline including a first subsegment, a second subsegment, and a flex circuit, wherein the first subsegment, when viewed in an axial direction along the central axis, extends along a linear path in a radial direction between a distal intersection at the central axis and a distal subsegment end of the second subsegment, wherein the second subsegment has a uniform cross-sectional area and, when viewed in the axial direction along the central axis, undulates along a curvilinear path having a plurality of localized bends bending in different directions between the distal subsegment end and a proximal subsegment end of the second subsegment, and wherein the flex circuit includes a plurality of electrodes and the flex circuit is wrapped around a circumference of an outer surface of the spline.

11. The electrophysiology catheter of claim 10, wherein the second subsegment undulates about the central axis along the curvilinear path.

12. The electrophysiology catheter of claim 10, wherein the spline includes a third subsegment, wherein a third top-down profile of the third subsegment viewed in the axial direction along the central axis is straight between the proximal subsegment end of the second subsegment and the central axis.

13. The electrophysiology catheter of claim 10 further comprising a reference electrode mounted on a non-tissue-contacting surface of the expandable member.

14. The electrophysiology catheter of claim 10, wherein a first portion of the spline has a different radiopacity than a second portion of the spline.

15. An electrophysiology catheter system, comprising:
a catheter shaft extending along a central axis between a proximal end and a distal end;
an expandable member mounted on the distal end, the expandable member including a spline extending continuously between a pair of proximal locations on the catheter shaft and intersecting at the central axis, the spline including a first subsegment, a second subsegment, and a flex circuit, wherein the first subsegment, when viewed in an axial direction along the central axis, extends along a linear path in a radial direction between a distal intersection at the central axis and a distal subsegment end of the second subsegment, wherein the second subsegment has a uniform cross-sectional area and, when viewed in the axial direction along the central axis, undulates along a curvilinear path having a plurality of localized bends bending in different directions between the distal subsegment end and a proximal subsegment end of the second subsegment, and wherein the flex circuit includes a plurality of electrodes and the flex circuit is wrapped around a circumference of an outer surface of the spline; and
a handle coupled to the proximal end of the catheter shaft.

16. The electrophysiology catheter system of claim 15, wherein the second subsegment undulates about the central axis along the curvilinear path.

17. The electrophysiology catheter system of claim 15, wherein the spline includes a third subsegment, wherein a third top-down profile of the third subsegment viewed in the axial direction along the central axis is straight between the proximal subsegment end of the second subsegment and the central axis.

18. The electrophysiology catheter system of claim 15 further comprising a reference electrode mounted on a non-tissue-contacting surface of the expandable member.

19. The electrophysiology catheter system of claim 15, wherein a first portion of the spline has a different radiopacity than a second portion of the spline.

20. The electrophysiology catheter system of claim 15 further comprising:
an electrode on the spline; and
a reference electrode on the catheter shaft.

\* \* \* \* \*